United States Patent [19]
Mutterer

[11] 3,956,340
[45] May 11, 1976

[54] PROCESS FOR THE PRODUCTION OF POLYHALOGENATED NICOTINIC ACIDS
[75] Inventor: Francis Mutterer, St. Louis, France
[73] Assignee: Ciba-Geigy Corporation, Ardsley, N.Y.
[22] Filed: Mar. 13, 1974
[21] Appl. No.: 450,933

[30] Foreign Application Priority Data
Apr. 4, 1973 Switzerland.......................... 4797/73

[52] U.S. Cl........................................ 260/295.5 R
[51] Int. Cl.$^2$...................................... C07D 213/80
[58] Field of Search ............................ 260/295.5 R

[56] References Cited
UNITED STATES PATENTS
2,657,207  10/1953  Herring, Jr.................. 260/295.5 R
3,278,592  10/1966  Moell et al........................ 260/524

FOREIGN PATENTS OR APPLICATIONS
1,317,667  1/1963  France

OTHER PUBLICATIONS
Binns et al., *Chemical Communications*, (1969), pp. 1211–1212.

Primary Examiner—Henry R. Jiles
Assistant Examiner—R. W. Ramsuer
Attorney, Agent, or Firm—Luther A. R. Hall

[57] ABSTRACT

A novel process for preparing 2,6-dichloro- and 2,5,6-trichloronicotinic acid is disclosed which comprises reacting 2,6-dichloro-3-chloromethylpyridine and 2,5,6-trichloro-3-chloromethylpyridine, respectively, with concentrated nitric acid in the presence of concentrated sulphuric acid and a metal salt catalyst. This process is both simple and economical; it is distinguished by high yields and low reaction temperatures while avoiding undesirable side-reactions.

8 Claims, No Drawings

PROCESS FOR THE PRODUCTION OF POLYHALOGENATED NICOTINIC ACIDS

The present invention relates to a new process for the manufacture of 2,6-dichloronicotinic acid and 2,5,6-trichloronicotinic acid.

It is known to manufacture pyridinecarboxylic acids by oxidation of alkylpyridines. Dilute nitric acid, for example, is used as the oxidising agent for this purpose, the reaction having to be carried out under pressure. The catalytic oxidation of alkylpyridines with sulphuric acid in the presence of selenium catalysts or metal salt catalysts is more advantageous. This process is carried out at about 280°–300°C. The conversion of alkylpyridines, such as β-picoline or γ-picoline, to pyridinecarboxylic acids by oxidation with 50–75% strength nitric acid in the presence of sulphuric acid and of metal salt catalysts has also already been described; this requires temperatures of 250°–260°C. However, none of the processes mentioned are suitable for the manufacture of nicotinic acids which are halogenated in the 2- and 6-position since under the reaction conditions mentioned a hydrolysis of the halogen atoms, coupled with extensive decomposition of the substances, occurs.

For this reason it has hitherto only been possible to manufacture 2,6-dichloronicotinic acid by an involved and expensive process, namely by condensation of isaconitic acid triethyl ester with ammonia and subsequent chlorination of the resulting 2,6-dihydroxynicotinic acid ethyl ester with a mixture of phosphorus pentachloride and phosphorus oxychloride [*Journal f. praktische Chemie* 58, 418–426 (1898)]. 2,5,6-Trichloronicotinic acid was hitherto unknown, because of the lack of a suitable process of manufacture.

It has now been found that polychloronicotinic acids of the formula I

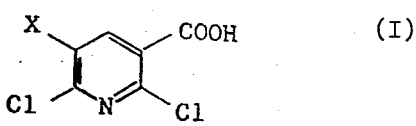

in which X can be hydrogen or chlorine, can be manufactured by reacting polychloro-3-chloromethylpyridines of the formula II

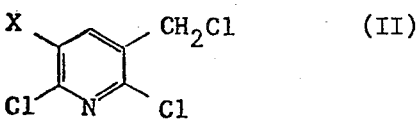

in which X has the same meaning as in the formula I, with highly concentrated nitric acid, which contains at least 90% by weight of $HNO_3$, in the presence of concentrated sulphuric acid and of metal salt catalysts at temperatures of 100° to 160°C, preferably at temperatures of 120° to 150°C. As highly concentrated nitric acid it is possible to use, above all, commercially available so-called "fuming nitric acid" which contains about 98% by weight of $HNO_3$ and has a density ($d_4^{20}$) of 1.5. The higher is the concentration of $HNO_3$, the more advantageously does the process take place. Suitable concentrated sulphuric acid in the sense of the process is commercial concentrated sulphuric acid containing about 96% by weight of $H_2SO_4$. The sulphuric acid acts essentially as a solvent. Its amount is generally not critical. The nitric acid is advantageously used in amounts of about 2 to 5 parts by weight per part by weight of starting compound of the formula II. Examples of suitable metal salt catalysts are vanadium compounds and selenium compounds, but above all mixtures of copper salts and mercury salts. The nature of the anion is virtually immaterial; thus, for example, acetates, nitrates, sulphates or chlorides can be used. Instead of a mixture of copper salts and mercury salts it is also possible to employ, with advantage, mixtures of copper compounds and mercury compounds which form the corresponding salts under the reaction conditions, for example the corresponding metal oxides or metal hydroxides. The use of a mixture of mercury nitrate and copper sulphate is particularly preferred. For economic reasons, the amount of the catalyst will be kept as low as possible; preferably, 0.02 to 0.1 part by weight of catalyst is used per part by weight of starting compound of the formula II.

The advantage of the process according to the invention is that it is possible to work at lower temperatures than in the known processes, and avoid hydrolytic reactions. An oxidation of alkylpyridines with highly concentrated nitric acid under practically anhydrous conditions has hitherto not been carried out because under these conditions the danger of a nitration is too great. It was therefore surprising that the chloromethylpyridines of the formula II can be oxidised with highly concentrated nitric acid without nitration occurring.

The 2,6-dichloro-3-chloromethylpyridine used as the starting product can be obtained by reacting 3-chloro-3-chloromethylglutarimide, which is obtainable, for example, by chlorination of α-methyleneglutaronitrile and cyclisation of the resulting 1,2-dichloro-2,4-dicyanobutane in an acid medium, with phosphorus oxychloride at a temperature between about 140° and 180°C. 2,5,6-Trichloro-3-chloromethylpyridine can be prepared by reaction of 3-chloro-3-chloromethylglutarimide with phosphorus pentachloride at a temperature of at most 75°C to give 3,5,6-trichloro-3-chloromethyl-5,6-dehydropiperidon-2-one followed by treatment of the latter with phosphorus oxychloride at a temperature between 160° and 200°C.

For the reaction, these chloromethylpyridines, preferably together with the catalyst, are dissolved in the concentrated sulphuric acid and the highly concentrated nitric acid is slowly added at temperatures of 100° to 160°C, preferably at 120° to 150°C.

The end products are isolated according to customary methods, for example by diluting the reaction mixture with water or a water-ice mixture and filtering off the polychloronicotinic acids which have separated out. The purity of the products thus obtained is adequate for most purposes. If further purification is necessary, this can be effected by recrystallisation from water.

The polychloronicotinic acids obtainable according to the invention are solid crystalline substances which are soluble in aqueous alkali and in various organic solvents, such as methanol, ethanol, diethyl ether, dioxane, acetone and N,N-dimethylformamide. The compounds can be used for the manufacture of pharmaceutical preparations. Thus, for example, the use of 2,6-dichloronicotinic acid as an intermediate product for the manufacture of hypolipidemic substances is described in German Offenlegungsschriften 2,157,289 and 2,157,334.

EXAMPLE 1

[Structure: pyridine with COOH at 3-position, Cl at 2 and 6 positions]

100 g (0.51 mol) of 2,6-dichloro-3-chloromethylpyridine, 500 g of 97% strength sulphuric acid, 5 g of $Hg(NO_3)_2$ and 2.5 g of $CuSO_4·5H_2O$ are warmed to 120°C, whilst stirring vigorously, in a 2.5 liter sulphonation flask equipped with a stirrer, thermometer and gas outlet tube. 190 ml (280 g) of fuming nitric acid are then added dropwise over the course of 3.5 hours in such a way that the internal temperature does not exceed 150°C. After completion of the addition of $HNO_3$, the reaction mixture is cooled to 40°C and poured onto 600 g of ice, whilst stirring. After half an hour, the acid which has precipitated is filtered off, well pressed out and suspended in 500 ml of water. The acid is then dissolved at pH 10 by adding $Na_2CO_3$. The resulting, somewhat turbid solution is filtered and strongly acidified with concentrated hydrochloric acid, whereupon 2,6-dichloronicotinic acid again precipitates. It is filtered off and dried. 72 g of pure 2,6-dichloronicotinic acid (74% of theory) of melting point 146°–148°C are obtained.

Analysis for $C_6H_3O_2Cl_2N$ (molecular weight 192):
Calculated: C, 37.53 H, 1.57 Cl, 36.93 N, 7.30%.
Found: C, 37.21 H, 1.52 Cl, 36.66 N, 7.24%.

The 2,6-dichloro-3-chloromethylpyridine used as the starting product in the above example can be manufactured as follows:

588 g (3 mols) Of 3-chloro-3-chloromethylglutarimide (obtained by chlorination of α-methyleneglutaronitrile, to form 1,2-dichloro-2,4-dicyanobutane, followed by cyclisation of the latter to form 3-chloro-3-chloromethylglutarimide, according to methods which are in themselves known) and 3 liters of phosphorus oxychloride are introduced into a 6 liter tantalum autoclave and heated to 160°C over the course of 3 hours. The resulting brown-colored solution is then freed of the phosphorus oxychloride in a rotary evaporator and the black-coloured oily residue, whilst still hot, is poured into a mixture of approx. 3 liters of ice and water. The ice/water mixture is stirred for approx. 4 hours until a light brown crystal suspension has been produced. The crystals are filtered off and repeatedly washed with water. The crystals are then again filtered off and dried in a vacuum drying cabinet at 25°C over diphosphorus pentoxide.

EXAMPLE 2

[Structure: pyridine with COOH at 3-position, Cl at 2, 5, and 6 positions]

115.5 g (0.50 mol) of 2,5,6-trichloro-3-chloromethylpyridine, 500 g of 97% strength sulphuric acid, 5 g of $Hg(NO_3)_2$ and 2.5 g of $CuSO_4·5H_2O$ are introduced into a 2.5 liter sulphonation flask of the type described in Example 1, and warmed to 110°C in an oil bath, whilst stirring vigorously. 150 ml (230 g) of fuming nitric acid are then added dropwise over the course of 1.5 hours. For the first 45 minutes, the reaction is not exothermic. After 50 to 60 minutes, that is to say after about 100 ml of $HNO_3$ have been added dropwise, the reaction solution turns dark brown and the reaction becomes exothermic. As soon as the internal temperature has reached 120°C, the oil bath is removed and replaced by ice water cooling, in such a way that the internal temperature does not exceed 130°–140°C. After completion of the addition of $HNO_3$, the reaction solution is cooled to 40°C and poured onto 800 g of ice. The acid which precipitates is filtered off, well pressed out and dried in a vacuum drying cabinet at 40°C. 90 g (79.5% of theory) of crude 2,5,6-trichloronicotinic acid of melting point 164°–168°C are obtained. Recrystallisation of the crude product from water gives pure 2,5,6-trichloronicotinic acid in 86% yield.

Analysis for $C_6H_2O_2Cl_3N$ (molecular weight 226.5):
Calculated: C, 31.89 H, 0.89 Cl, 47.06 N, 6.20%.
Found: C, 31.55 H, 1.09 Cl, 46.74 N, 6.29%.

The 2,5,6-trichloro-3-chloromethylpyridine used as the starting product in the above example can be manufactured as follows:

82.8 g (0.333 mol) of 3,5,6-trichloro-3-chloromethyl-5,6-dehydro-piperidin-2-one (obtained by reaction of 3-chloro-3-chloromethylglutarimide with phosphorus pentachloride at a temperature of 70°–71°C) and 400 ml (4.4 mols) of phosphorus oxychloride are heated to 180°C over the course of 3 hours in an autoclave. The excess phosphorus oxychloride is then removed from the reaction solution on a rotary evaporator and the dark brown-coloured residue is poured onto ice. The crystals which separate out are filtered off, washed with water and dried overnight over diphosphorus pentoxide.

What is claimed is:
1. A process for the manufacture of 2,6-dichloronicotinic acid which comprises oxidizing 2,6-dichloro-3-chloromethylpyridine by reaction with highly concentrated nitric acid containing at least 90% by weight of $HNO_3$, in the presence of concentrated sulphuric acid and of a catalyst selected from the group consisting of salts of vanadium, selenium, copper and mercury, at temperatures of 100° to 160°C.

2. A process according to claim 1, characterised in that fuming nitric acid is used.

3. A process according to claim 1, characterised in that about 2 to 5 parts by weight of nitric acid are used per part by weight of starting compound 2,6-dichloro-3-chloromethylpyridine.

4. A process according to claim 1 wherein the catalyst is selected from the group consisting of the acetates, nitrates, sulphates and chlorides of vanadium, selenium, copper and mercury or from the group consisting of the oxides and hydroxides of vanadium, selenium, copper and mercury which form the corresponding nitrate and sulphate salts under reaction conditions.

5. A process according to claim 1 wherein the catalyst is a mixture of copper and mercury salts selected from the group consisting of the acetates, nitrates, sulphates and chlorides of copper and mercury, or from the group consisting of the oxides and hydroxides of copper and mercury which form the corresponding nitrate and sulphate salts under reaction conditions.

6. A process according to claim 1, characterised in that a mixture of mercury nitrate and copper sulphate is used as the catalyst.

7. A process according to claim 1, characterised in that the catalyst is employed in an amount of 0.02 to 0.1 part by weight per part by weight of starting compound 2,6-dichloro-3-chloromethylpyridine.

8. A process according to claim 1, characterised in that the oxidation is carried out at 120° to 150°C.

* * * * *